US012642290B2

(12) United States Patent
Samuel et al.

(10) Patent No.: US 12,642,290 B2
(45) Date of Patent: Jun. 2, 2026

(54) FOOD COMPOSITIONS FOR WEIGHT MANAGEMENT

(71) Applicant: SOCIETE DES PRODUITS NESTLE S.A., Vevey (CH)

(72) Inventors: Tinu Mary Samuel, La Tour de Peilz (CH); Dantong Wang, Prilly (CH); Mathilde Fleith, Saint-Legier (CH); Colleen Fogarty Draper, St Sulpice (CH)

(73) Assignee: Societe des Produits Nestle S.A., Vevey (CH)

( * ) Notice: Subject to any disclaimer, the term of this patent is extended or adjusted under 35 U.S.C. 154(b) by 846 days.

(21) Appl. No.: 17/597,526

(22) PCT Filed: Jul. 8, 2020

(86) PCT No.: PCT/EP2020/069188
§ 371 (c)(1),
(2) Date: Jan. 10, 2022

(87) PCT Pub. No.: WO2021/005088
PCT Pub. Date: Jan. 14, 2021

(65) Prior Publication Data
US 2022/0248740 A1 Aug. 11, 2022

(30) Foreign Application Priority Data
Jul. 11, 2019 (EP) ..................................... 19185652

(51) Int. Cl.
| | |
|---|---|
| *A23L 33/00* | (2016.01) |
| *A23L 33/15* | (2016.01) |
| *A23L 33/16* | (2016.01) |
| *A23L 33/21* | (2016.01) |
| *A61K 31/015* | (2006.01) |
| *A61K 31/375* | (2006.01) |
| *A61K 31/51* | (2006.01) |
| *A61K 31/519* | (2006.01) |
| *A61K 33/06* | (2006.01) |
| *A61K 33/30* | (2006.01) |
| *A61P 3/02* | (2006.01) |

(52) U.S. Cl.
CPC .............. *A23L 33/30* (2016.08); *A23L 33/15* (2016.08); *A23L 33/16* (2016.08); *A23L 33/21* (2016.08); *A23L 33/40* (2016.08); *A61K 31/015* (2013.01); *A61K 31/375* (2013.01); *A61K 31/51* (2013.01); *A61K 31/519* (2013.01); *A61K 33/06* (2013.01); *A61K 33/30* (2013.01); *A61P 3/02* (2018.01); *A23V 2002/00* (2013.01)

(58) Field of Classification Search
None
See application file for complete search history.

(56) References Cited

U.S. PATENT DOCUMENTS

| | | | |
|---|---|---|---|
| 2006/0088574 A1 | 4/2006 | Manning et al. | |
| 2006/0275506 A1 | 12/2006 | Fisher et al. | |
| 2009/0142314 A1 | 6/2009 | Haschke et al. | |
| 2010/0178281 A1* | 7/2010 | Salminen ............. | A61K 35/741 424/93.4 |
| 2011/0305642 A1* | 12/2011 | Gervais ..................... | A61P 3/02 424/646 |
| 2016/0050962 A1 | 2/2016 | Davies et al. | |

FOREIGN PATENT DOCUMENTS

| | | | |
|---|---|---|---|
| CN | 106983136 | | 7/2017 |
| CN | 107 156 820 | * | 9/2017 |
| EP | 2614725 A1 | | 7/2013 |
| WO | 9953777 | | 10/1999 |
| WO | 2014016627 A1 | | 1/2014 |
| WO | 2016035095 A1 | | 3/2016 |

OTHER PUBLICATIONS

Bertz et al. "Sustainable Weight Loss among overweight and Obese Lactating Women is achieved with an Energy-Reduced Diet in line with Dietary Recommendations: Results from the LEVA Randomized Controlled trial".*
Wang, "Bodybuilding and Weight Loss", Nov. 2020, p. 127.
Chinese Office Action for Appl No. 202080052222.1 dated Nov. 12, 2024, 9 pages.
Chinese Office Action for Appl No. 202080052222.1 dated Sep. 7, 2023.
Wang et al., "Common Disease Nursing Practice and Operation Routine", Jun. 30, 2020, p. 106.
Office Action Received for Application No. CN202080052222.1, mailed on Jul. 25, 2024, 21 Pages (11 Pages of English Translation and 10 Pages of Official Copy).
Wang et al., "Analysis of Dietary Patterns and Nutritional Adequacy in Lactating Women: A Multicentre European Cohort (Atlas Study)", Journal of Nutritional Science, vol. 10, Issue No. e17, 2021, pp. 1-10.
Drehmer et al., "Fibre Intake and Evolution of BMI: From Pre-pregnancy to Postpartum", Public Health Nutrition, vol. 16, Issue No. 08, 2012, pp. 1403-1413.
"Bodyaction Whey Pro-F Suplemento Proteico Para Atletas Sabor Chocolate: Chocolate Flavored Whey Protein Supplement for Athletes", Innova Market Insights, Product ID 3817071, Mar. 2016, 2 Pages.
"Product: Metabolic Reset Vanilla", National Institutes of Health Office of Dietary Supplements, 2015, pp. 1-10.
"Supplementary Material for Analysis of Dietary Patterns and Nutritional Adequacy in Lactating Women: A Multicentre European Cohort (Atlas Study)", Journal of Nutritional Science, 2021, pp. 1-4.
"Tomatoes, Red, Ripe, Raw, Year Round Average", USDA Food Data Central Database for Tomatoes, 2019, 14 Pages.

(Continued)

Primary Examiner — Danah Al-Awadi
(74) Attorney, Agent, or Firm — K&L Gates LLP

(57) ABSTRACT

The present invention concerns a food composition comprising at least one of fiber, beta-carotene, folate, magnesium, zinc, vitamin C, and thiamin, for use in assisting in post-partum weight management.

7 Claims, 4 Drawing Sheets

(56)  References Cited

OTHER PUBLICATIONS

"Medical Nutritional Products", Ross - Nutrition Product Guide, 60 Pages.

European Office Action for Appl No. 20735628.8 - 1105 dated Mar. 16, 2026, 15 pages.

Kumarasinghe et al., "Postpartum Versus Postnatal Period: Do the Name and Duration Matter?", Plos One, vol. 19, Apr. 26, 2024, 14 Pages.

Kolasa et al., "Nutrition During Pregnancy and Lactation", Handbook of Nutrition and Food, 2009, pp. 235-257.

Whigam et al., "Efficacy of Conjugated Linoleic Acid for Reducing Fat Mass: A Meta-analysis in Humans,", American Society for Nutrition, vol. 85, 200, pp. 1203-1211.

Gui et al., "Chemistry Encapsulatio, and Health Benefits of β-carotene—a Review", Cogent Food & Agriculture, Mar. 10, 2015, vol. No. 1, 13 Pages.

European Office Action for Appl. No. 20735628.8-1105 dated Mar. 26, 2026, 39 pages.

* cited by examiner

Figure 1
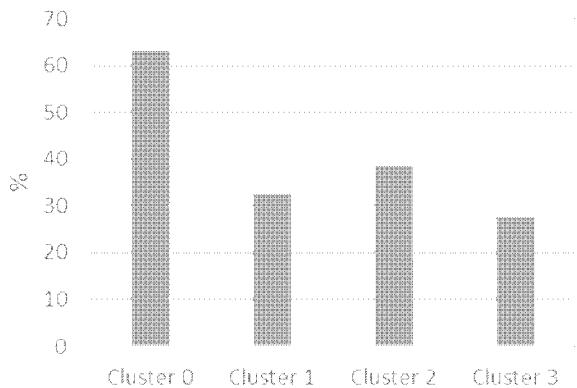
Figure 2
Figure 2a
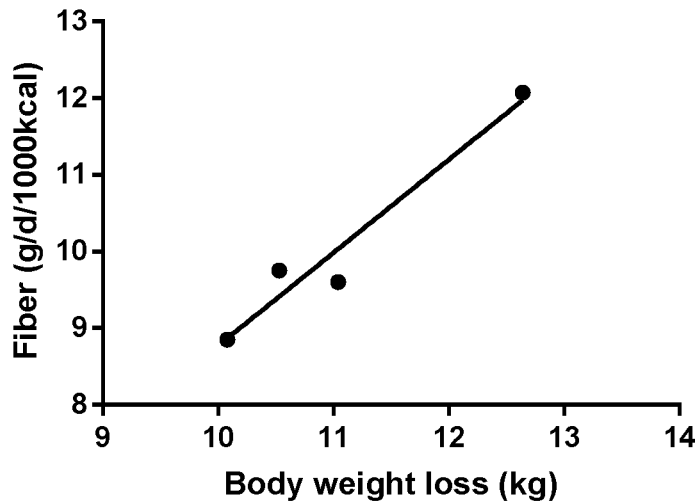

FOOD COMPOSITIONS FOR WEIGHT MANAGEMENT

CROSS REFERENCE TO RELATED APPLICATIONS

The present application is a National Stage of International Application No. PCT/EP2020/069188, filed on Jul. 8, 2020, which claims priority to European Patent Application No. 19185652.5, filed on Jul. 11, 2019, the entire contents of which are being incorporated herein by reference.

FIELD OF THE INVENTION

The present invention concerns a food composition assisting in post-partum weight management.

BACKGROUND OF THE INVENTION

Overweight and obesity is prevalent among women of reproductive age (25-34 years) with 42% having a body mass index (BMI)>25 kg/m². Having children is associated with maternal weight gain, particularly in the long-term. Fifty to eighty percent of women retain 1.4-5 kg up to 12 months postpartum, with 20%-50% retaining 5 kg or more. Weight gain increases the risk of developing diabetes and heart disease. The amount of weight retained after pregnancy can shift women from the healthy weight category into the overweight or obese BMI categories. Starting the next pregnancy at a higher weight increases the risk for poor pregnancy outcomes, such as gestational diabetes, delivery intervention, macrosomia and lower rates of breastfeeding initiation and duration. Women with a high BMI have been reported to have a 7% lower breastfeeding initiation rate and breastfeed for six weeks less on average, compared to women with a normal BMI. This may likely be due to the physical size of the breast and diminished lactogenesis (Martin et al. Nutrients. 2015 March; 7(3): 1464-1479).

There is thus evidence suggesting that post-partum weight retention is an issue for the general health status of the woman as well as for future pregnancies and breastfeeding outcomes. During breast feeding, the process of lactation adds to energy expenditure, and therefore could assist with weight loss in the postpartum period until the kid reaches the age of 6 months up to when exclusive breastfeeding is recommended by WHO.

Anyway, when the infant reaches the age of 6 months and complementary feeding starts to be introduced in his diet, lactation diminishes and so does the associated energy expenditure. Accordingly, there is a need when complementary feeding starts for infants to assist their mothers in weight loss during extended, but partial lactation and/or when lactation stops. There is also a need to enrich diet of the mother in nutrients which may contribute to extend lactation as long as possible, ideally until two years as recommended by WHO; for example by providing the right nutrients that are transferred through breast milk to provide adequate nutrition.

Accordingly, it is an object of the present invention to provide a food composition assisting in post-partum weight management, especially from 6 months after delivery onwards.

SUMMARY OF THE INVENTION

The present inventions provides a solution to the above mentioned problem as set out in the claims.

BRIEF DESCRIPTION OF THE DRAWINGS

Additional features and advantages of the present invention are described in, and will be apparent from, the description of the presently preferred embodiments which are set out below with reference to the drawings in which:

FIG. 1 is a representation of the proportion of subjects showing high body weight loss in clusters 0, 1, 2 and 3 as defined in Example 1 of the present invention.

FIG. 2a, 2b, 2c, 2d, 2e, 2f, 2g report the correlation between Mean Body weight loss over visits V2-V6 and energy adjusted amounts of, respectively, the following ingredients in the 4 clusters of dietary patterns observed: fibre, folate, beta-carotene, magnesium, Thiamin, zinc and Vitamin C.

DETAILED DESCRIPTION OF THE INVENTION

Definitions

Figure 2B:
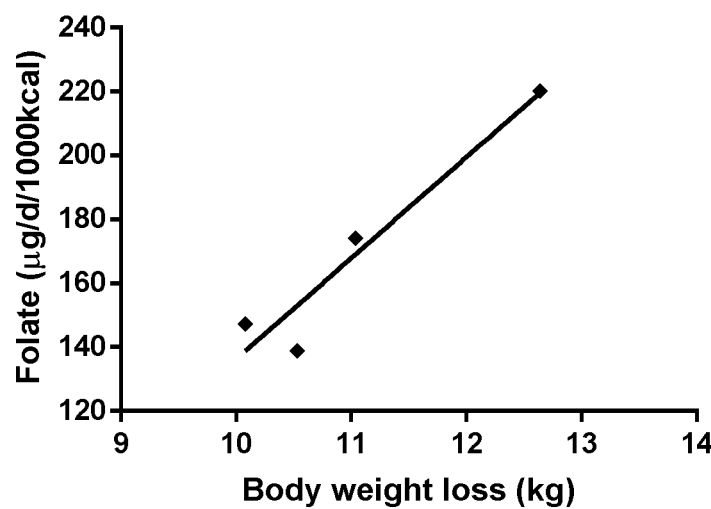

Prior to discussing the present invention in further details, the following terms and conventions will first be defined.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 1 to 10 (including 1 and 10), from 2 to 8, from 3 to 7, from 1 to 9, from 3.6 to 4.6, from 3.5 to 9.9, and so forth. All references to singular characteristics or limitations of the present invention shall include the corresponding plural characteristic or limitation, and vice versa, unless otherwise specified or clearly implied to the contrary by the context in which the reference, is made.

The term "and/or" used in the context of the "X and/or Y" should be interpreted as "X", or "Y", or "X and Y".

Unless defined otherwise, all technical and scientific terms used herein have the same meaning as commonly understood by one of ordinary skilled in the art.

Within the context of the present invention, the term "nutrient" or nutrients" is intended to comprise both macro-nutrients (for example carbohydrates, proteins or fats) and micronutrients (for example minerals or vitamins) for the human body.

Within the context of the present invention, the term "ingredient" or "ingredients" indicates an edible substance or mixture of substances which comprise or is essentially consisting of a nutrient for the human body.

In one embodiment of the present invention, the term "ingredient" or "ingredients" indicates an edible substance essentially consisting of a nutrient for the human body.

Within the context of the present invention, the term "ingredient providing nutrient X" or "ingredients providing nutrient X" indicates an edible substance and/or mixture of substances which comprise or is essentially consisting of at least one substance capable of delivering the specified nutrient X to the human body.

Within the context of the present invention, the term "ingredient providing nutrient X in amount Y" or "ingredients providing nutrient X in amount Y" indicates an edible substance and/or mixture of substances which comprise or is essentially consisting of at least one substance capable of delivering the specified nutrient X to the human body in the specified amount Y.

The expressions "fiber" or "fibers" or "dietary fiber" or "dietary fibers" within the context of the present invention indicate the indigestible portion, in small intestine, of food derived from plants which comprises two main components: Soluble fiber, which dissolves in water, and insoluble fiber. Mixtures of fibers are comprised within the scope of the terms above mentioned. Soluble fiber is readily fermented in the colon into gases and physiologically active byproducts, and can be prebiotic and viscous. Insoluble fiber does not dissolve in water, is metabolically inert and provides bulking, or it can be prebiotic and metabolically ferment in the large intestine. Chemically, dietary fiber consists of non-starch polysaccharides (NPS) such as arabinoxylans, cellulose, and many other plant components such as resistant oligosaccharides, resistant starch, resistant dextrins, inulin, lignin, chitins, pectins, beta-glucans, and oligosaccharides. Non limiting examples of dietary fibers are: prebiotic fibers such as Fructo-oligosaccharides (FOS), inulin, galacto-oligosaccharides (GOS), fruit fiber, legume fiber, vegetable fiber, cereal fiber, resistant starch such as high amylose corn starch. As fibers are not digestible, they do not contain available carbohydrates.

Within the context of the present invention the term "added fiber" or "added dietary fiber" indicates an ingredient mainly or totally constituted by fiber which is added to the food composition according to the present invention and whose content in fiber contributes to the total fiber content of the composition. The total fiber content of the food composition is provided by the sum of amount of fiber naturally present in ingredients used in the recipe (for example from whole grain cereal flour) plus amount of added fiber.

Within the context of the present invention, the term "legume" or "legumes" identifies the fruit or seed of a plant in the family of Fabaceae or mixtures thereof. Well-known legumes include inter alia alfalfa, clover, peas, beans, lentils, lupins, mesquite, carob, soybeans, peanuts and tamarind. The grain seeds of such plants are generally known as "pulses" and are comprised within the scope of the term "legumes" according to the present invention.

Within the context of the present invention, the term "fruit" or "fruits" indicates ingredients derived from fruit such as for example fresh fruit, fruit paste, dried fruit, fruit extracts and/or centrifugates. Mixtures of such ingredients are also comprised within the scope of the terms above mentioned. Non limiting examples of fruit according to the present invention are: apple, apricot, banana, cherry, pear, strawberry, Mango, Orange, peach.

As it will be apparent to the skilled person, legumes and fruit according to the present invention may bring certain amount of fibers to the food composition of the present invention.

Within the context of the present invention, the term "assisting in post partum weight management" or "assisting in post partum weight loss" means reducing body weight gain, improving and/or enhancing body weight loss, preventing post partum weight retention, or treating and/or preventing overweight and/or obesity in the women who gave birth, in particular when exclusive breast feeding is interrupted or breast feeding is reduced or stopped, for example starting from 6 or 4 months after giving birth onwards.

Within the context of the present invention, the term "food composition" identifies an edible composition suitable for human ingestion. Non limiting examples of food composition may be selected from the group consisting of a powdered nutritional composition to be reconstituted in milk or water, a powdered nutritional composition stored in a single use capsule or pod to be reconstituted in milk or water, a nutritional formula, a cereal based-product, a drink, a bar, a nutritional supplement, a maternal supplement, a nutraceutical, a yogurt, a dairy based product, a food sprinkler, a gummy, a meal replacer, a pill or a tablet.

Within the context of the present invention, the term "serving" indicates one portion or serving unit of the food composition according to the present invention. The appropriate serving size would be apparent to the person skilled in the art for each type of food composition and could be retrieved either from applicable nutritional recommendation and/or from indications on the product packaging.

In one embodiment, the term "serving" indicates a serving unit, for example as indicated on the product packaging.

In one embodiment, when the food composition is a supplement which only contains excipients on top of zinc, magnesium, folates, vitamin C, thiamin, beta-carotene and/or fibres, the term serving indicates a serving unit.

The composition of the present invention, including the many embodiments described herein, can comprise, consist of, or consist essentially of the essential elements and limitations of the invention described herein, as well as any additional or optional ingredients, components, or limitations described herein.

Food Composition

In one embodiment, the food composition according to the present invention comprises at least one ingredient selected in the group consisting of: zinc, magnesium, folates, vitamin C, thiamin, beta-carotene and fibres.

In another embodiment, the food composition according to the present invention comprises at least two ingredients selected in the group consisting of: zinc, magnesium, folates, vitamin C, thiamin, beta-carotene and fibres.

In another embodiment, the food composition according to the present invention comprises at least three ingredients selected in the group consisting of: zinc, magnesium, folates, vitamin C, thiamin, beta-carotene and fibres.

In a further embodiment, the food composition according to the present invention comprises magnesium, folates, beta-carotene and fibres.

In a further embodiment, the food composition according to the present invention comprises zinc, magnesium, folates, vitamin C, and fibres.

Food compositions according to the present invention may comprise additional ingredients such as proteins, fats, carbohydrates, prebiotics, probiotics, other vitamins and/or minerals.

In one embodiment, the food composition of the present invention also comprises Calcium. In such embodiment, Calcium may also assist in body weight loss.

In one embodiment, the food composition of the present invention also comprises Vitamin E and/or Vitamin B6. In such embodiment, Vitamin E and/or Vitamin B6 may also assist in body weight loss.

In one embodiment, the food composition of the present invention also comprises conjugated Linolenic acid (CLA) glycerides. In such embodiment, conjugated Linolenic acid (CLA) glycerides may also assist in body weight loss.

In one additional embodiment, the food composition of the present invention also comprises conjugated Linolenic acid (CLA) glycerides, Vitamin E, Vitamin B6, calcium and has a protein content higher than 15 g, for example higher than 20 g, of protein per 100 g of food composition in a powder form.

The maternal food composition may have any form that is accepted by women as part of their diet or as nutritional supplement.

For example, the food composition according to the present invention may be selected from the group consisting of a powdered nutritional composition to be reconstituted in milk or water, a powdered nutritional composition stored in a single use capsule or pod to be reconstituted in milk or water, a nutritional formula, a cereal based-product, a drink, a bar, a nutritional supplement, ametrenal supplement, a nutraceutical, a yogurt, a dairy based product, a food sprinkler, a gummy, a meal replacer, a pill or a tablet.

In one embodiment, the food composition according to the present invention is a dairy based product, for example a liquid dairy based product or a powdered dairy based product to be reconstituted in milk or water.

In one embodiment, particularly well accepted by consumers are powdered nutritional compositions to be reconstituted in milk or water.

In another embodiment, also well accepted are nutritional supplements, for example in the form of a tablet or a gummy. The supplement provides selected nutrients while not representing a significant portion of the overall nutritional needs of the subject and/or does not represent more than 0.1%, 1%, 5%, 10%, or 20% of the daily energy need of the subject.

In one embodiment of the present invention, the food composition has a high protein content, for example a protein content higher than 15 g, for example higher than 20 g, of protein per 100 g of product in a powder form. In such embodiment, the high protein content of the food composition may also assist in body weight loss.

Zinc

In one embodiment of the present invention, a food composition is provided which comprises zinc.

Zinc may be incorporated in the composition of the invention as such or in the form of a physiologically acceptable salt and/or via any source comprising zinc. For example ingredients may be selected in the group consisting of: zinc acetate, zinc chloride, zinc citrate, zinc gluconate, zinc lactate, zinc oxide, zinc sulphate, zinc carbonate and mixtures thereof.

In one embodiment, zinc is provided by zinc sulphate to the food composition.

As it is evident to the person skilled in the art, different ingredients may provide different amounts of zinc in the composition according to the present invention, depending on the nature and amount of the ingredient used. It will be nonetheless routine work to the skilled person to calculate the amount of ingredient needed to provide the claimed amount of zinc, based on the specification of the specific ingredient provided by the supplier.

In one embodiment, the food composition of the present invention comprises zinc in an amount of at least 10.5 mg per serving, for example at least 11.0 mg per serving. In another embodiment, the food composition of the present invention comprises zinc in an amount ranging from 10.5 to 12.0 mg per serving. In a further embodiment, the food composition of the present invention comprises zinc in an amount ranging from 11.0 to 12.0 mg per serving.

In such embodiment, the food composition of the present invention delivers the daily amount of zinc considered responsible for the observed increase in body weight loss.

In one embodiment, the food composition of the present invention comprises zinc in an amount of at least 1.0 mg per serving, for example at least 1.1 mg per serving. In another embodiment, the food composition of the present invention comprises zinc in an amount ranging from 1.0 to 1.6 mg per serving. In a further embodiment, the food composition of the present invention comprises zinc in an amount ranging from 1.1 to 1.5 mg per serving.

In such embodiment, the food composition of the present invention delivers the daily amount of zinc resulting to be missing in the general population according to our study and necessary to reach levels associated with the observed increase in body weight loss.

In one embodiment, the food composition according to the present invention may be administered in 1, 2, 3 or 4 daily servings to provide the total daily amounts of zinc as above described. In such embodiment, as it will be apparent to a person skilled in the art, the amount of zinc contained in each serving of the food composition according to the present invention will be divided by 1, 2 3 or 4 respectively.

In one embodiment, the food composition according to the present invention is intended for consumption once or twice per day.

Vitamin C

In one embodiment of the present invention, a food composition is provided which comprises Vitamin C.

Vitamin C may be incorporated in the composition of the invention as such or in the form of a physiologically acceptable salt and/or via any source comprising Vitamin C. For example ingredients may be selected in the group consisting of: ascorbic acid, sodium ascorbate and mixtures thereof.

As it is evident to the person skilled in the art, different ingredients may provide different amounts of Vitamin C in the composition according to the present invention, depending on the nature and amount of the ingredient used. It will be nonetheless routine work to the skilled person to calculate the amount of ingredient needed to provide the claimed amount of Vitamin C, based on the specification of the specific ingredient provided by the supplier.

In one embodiment, the food composition of the present invention comprises Vitamin C in an amount of at least 125.0 mg per serving, for example at least 130.0 mg per serving. In another embodiment, the food composition of the present invention comprises Vitamin C in an amount ranging from 125.0 to 145.0 mg per serving. In a further embodiment, the food composition of the present invention comprises Vitamin C in an amount ranging from 130.0 to 140.0 mg per serving. In such embodiment, the food composition of the present invention delivers the daily amount of Vitamin C considered responsible for the observed increase in body weight loss.

In one embodiment, the food composition of the present invention comprises Vitamin C in an amount of at least 15 mg per serving, for example at least 17 mg per serving. In another embodiment, the food composition of the present invention comprises Vitamin C in an amount ranging from 15.0 to 25.0 mg per serving. In a further embodiment, the food composition of the present invention comprises Vitamin C in an amount ranging from 17.0 to 22.0 mg per serving. In such embodiment, the food composition of the present invention delivers the daily amount of Vitamin C resulting to be missing in the general population according to our study and necessary to reach levels associated with the observed increase in body weight loss.

In one embodiment, the food composition according to the present invention may be administered in 1, 2, 3 or 4 daily servings to provide the total daily amounts of Vitamin C as above described. In such embodiment, as it will be apparent to a person skilled in the art, the amount of Vitamin C contained in each serving of the food composition according to the present invention will be divided by 1, 2 3 or 4 respectively.

In one embodiment, the food composition according to the present invention is intended to be consumed once or twice per day.

Thiamin

In one embodiment of the present invention, a food composition is provided which comprises Thiamin.

Thiamin (Vitamin B1) may be incorporated in the composition of the invention as such or in the form of a physiologically acceptable salt and/or via any source comprising Thiamin. For example ingredients may be selected in the group consisting of: Vitamin B1 Hydrochloride and Vitamin B1 Mononitrate, or mixtures thereof.

As it is evident to the person skilled in the art, different ingredients may provide different amounts of Thiamin in the composition according to the present invention, depending on the nature and amount of the ingredient used. It will be nonetheless routine work to the skilled person to calculate the amount of ingredient needed to provide the claimed amount of Thiamin, based on the specification of the specific ingredient provided by the supplier.

In one embodiment, the food composition of the present invention comprises Thiamin in an amount of at least 1.6 mg per serving, for example at least 1.8 mg per serving. In another embodiment, the food composition of the present invention comprises Thiamin in an amount ranging from 1.6 to 2.4 mg per serving. In a further embodiment, the food composition of the present invention comprises Thiamin in an amount ranging from 1.8 to 2.3 mg per serving.

In such embodiment, the food composition of the present invention delivers the daily amount of Thiamin considered responsible for the observed increase in body weight loss.

In one embodiment, the food composition of the present invention comprises Thiamin in an amount of at least 0.40 mg per serving, for example at least 0.45 mg per serving. In another embodiment, the food composition of the present invention comprises Thiamin in an amount ranging from 0.40 to 0.65 mg per serving. In a further embodiment, the food composition of the present invention comprises Thiamin in an amount ranging from 0.45 to 0.60 mg per serving.

In such embodiment, the food composition of the present invention delivers the daily amount of Thiamin resulting to be missing in the general population according to our study and necessary to reach levels associated with the observed increase in body weight loss.

In one embodiment, the food composition according to the present invention may be administered in 1, 2, 3 or 4 daily servings to provide the total daily amounts of Thiamin as above described. In such embodiment, as it will be apparent to a person skilled in the art, the amount of Thiamin contained in each serving of the food composition according to the present invention will be divided by 1, 2 3 or 4 respectively.

In one embodiment, the food composition according to the present invention is intended to be consumed once or twice per day.

Beta-Carotene

In one embodiment of the present invention, a food composition is provided which comprises beta-carotene.

Beta-carotene may be incorporated in the composition of the invention as such or via any source comprising it. For example ingredients providing beta-carotene may be synthetic or natural sources.

As it is evident to the person skilled in the art, different ingredients may provide different amounts of beta-carotene in the composition according to the present invention, depending on the nature and amount of the ingredient used. It will be nonetheless routine work to the skilled person to calculate the amount of ingredient needed to provide the claimed amount of beta-carotene, based on the specification of the specific ingredient provided by the supplier.

In one embodiment, the food composition of the present invention comprises beta-carotene in an amount of at least 3.0 mg per serving, for example at least 3.2 mg per serving. In another embodiment, the food composition of the present invention comprises beta-carotene in an amount ranging from 3.0 to 4.5 mg per serving. In a further embodiment, the food composition of the present invention comprises beta-carotene in an amount ranging from 3.2 to 4.0 mg per serving.

In such embodiment, the food composition of the present invention delivers the daily amount of beta-carotene considered responsible for the observed increase in body weight loss.

In one embodiment, the food composition of the present invention comprises beta-carotene in an amount of at least 0.70 mg per serving, for example at least 0.75 mg per serving. In another embodiment, the food composition of the present invention comprises beta-carotene in an amount ranging from 0.70 to 0.95 mg per serving. In a further embodiment, the food composition of the present invention comprises beta-carotene in an amount ranging from 0.75 to 0.90 mg per serving.

In such embodiment, the food composition of the present invention delivers the daily amount of beta-carotene resulting to be missing in the general population according to our study and necessary to reach levels associated with the observed increase in body weight loss.

In one embodiment, the food composition according to the present invention may be administered in 1, 2, 3 or 4 daily servings to provide the total daily amounts of beta-carotene as above described. In such embodiment, as it will be apparent to a person skilled in the art, the amount of beta-carotene contained in each serving of the food composition according to the present invention will be divided by 1, 2 3 or 4 respectively.

In one embodiment, the food composition according to the present invention is intended to be consumed once or twice per day.

Magnesium

In one embodiment of the present invention, a food composition is provided which comprises magnesium.

Magnesium may be incorporated in the composition of the invention as such or in the form of a physiologically acceptable salt and/or via any source comprising magnesium, more specifically Mg2+. For example magnesium carbonate, magnesium chloride, magnesium oxide, magnesium sulphate, magnesium gluconate, magnesium hydroxide, magnesium salts of citric acid, magnesium salts of orthophosphoric acid.

In one embodiment, magnesium is provided via Magnesium oxide in the food composition.

As it is evident to the person skilled in the art, different ingredients may provide different amounts of magnesium in the composition according to the present invention, depending on the nature and amount of the ingredient used. It will be nonetheless routine work to the skilled person to calculate the amount of ingredient needed to provide the claimed amount of magnesium, based on the specification of the specific ingredient provided by the supplier.

In one embodiment, the food composition of the present invention comprises magnesium in an amount of at least 340 mg per serving, for example at least 350 mg per serving. In another embodiment, the food composition of the present invention comprises magnesium in an amount ranging from 340 to 430 mg per serving. In a further embodiment, the food composition of the present invention comprises magnesium in an amount ranging from 350 to 410 mg per serving. In such embodiment, the food composition of the present invention delivers the daily amount of magnesium considered responsible for the observed increase in body weight loss.

In one embodiment, the food composition of the present invention comprises magnesium in an amount of at least 40.0 mg per serving, for example at least 50.0 mg per serving. In another embodiment, the food composition of the present invention comprises magnesium in an amount ranging from 40.0 to 90.0 mg per serving. In a further embodiment, the food composition of the present invention comprises magnesium in an amount ranging from 50.0 to 80.0 mg per serving.

In such embodiment, the food composition of the present invention delivers the daily amount of magnesium resulting to be missing in the general population according to our study and necessary to reach levels associated with the observed increase in body weight loss.

In one embodiment, the food composition according to the present invention may be administered in 1, 2, 3 or 4 daily servings to provide the total daily amounts of magnesium as above described. In such embodiment, as it will be apparent to a person skilled in the art, the amount of magnesium contained in each serving of the food composition according to the present invention will be divided by 1, 2 3 or 4 respectively.

In one embodiment, the food composition according to the present invention is intended to be consumed once or twice per day.

Folate

In one embodiment of the present invention, a food composition is provided which comprises at least one ingredient which delivers folate.

Folate may be incorporated in the nutritional compositions of the invention as folic acid or in the form of a physiologically acceptable salt thereof (folate) or mixtures thereof.

In one embodiment, folate is of synthetic origin.

As it is evident to the person skilled in the art, different ingredients may provide different amounts of folate in the composition according to the present invention, depending on the nature and amount of the ingredient used. It will be nonetheless routine work to the skilled person to calculate the amount of ingredient needed to provide the claimed amount of folate, based on the specification of the specific ingredient provided by the supplier.

In one embodiment, the food composition of the present invention comprises folate in an amount of at least 350 µg per serving, for example at least 370 µg per serving. In another embodiment, the food composition of the present invention comprises folate in an amount ranging from 350 to 500 µg per serving. In a further embodiment, the food composition of the present invention comprises folate in an amount ranging from 370 to 480 µg per serving.

In such embodiment, the food composition of the present invention delivers the daily amount of folate considered responsible for the observed increase in body weight loss.

In one embodiment, the nutritional composition of the present invention comprises folate in an amount of at least 90.0 µg per serving, for example at least 100.0 µg per serving. In another embodiment, the nutritional composition of the present invention comprises folate in an amount ranging from 90.0 to 150 µg per serving. In a further embodiment, the nutritional composition of the present invention comprises folate in an amount ranging from 100.0 to 140.0 µg per serving.

In such embodiment, the food composition of the present invention delivers the daily amount of folate resulting to be missing in the general population according to our study and necessary to reach levels associated with the observed increase in body weight loss.

In one embodiment, the food composition according to the present invention may be administered in 1, 2, 3 or 4 daily servings to provide the total daily amounts of folate as above described. In such embodiment, as it will be apparent to a person skilled in the art, the amount of folate contained in each serving of the food composition according to the present invention will be divided by 1, 2 3 or 4 respectively.

In one embodiment, the food composition according to the present invention is intended to be consumed once or twice per day.

Dietary Fibres

In one embodiment of the present invention, a food composition is provided which comprises at least one ingredient which delivers fibres.

In one embodiment of the present invention, a food composition is provided which comprises fibres.

In one embodiment, the ingredients providing fibres may be capable of providing fibres of natural or synthetic origin.

In one embodiment, fibres of synthetic origin are for example FOS from sucrose.

In one embodiment, ingredients which are capable of providing dietary fibres are selected in the group consisting of: Fruit, Vegetable, Legume, Cereal and Cruciferous vegetable.

In one embodiment, dietary fibres are selected in the group consisting of: resistant dextrin, resistant oligosaccharides, NPS, resistant starches (for example pectine), polydextrose, inulin, partially hydrolyzed guar gum (PHGG), FOS, acacia gum, pea fiber, and mixtures thereof.

As it is evident to the person skilled in the art, different ingredients may provide different amounts of dietary fibres in the composition according to the present invention, depending on the nature and amount of the ingredient used. It will be nonetheless routine work to the skilled person to calculate the amount of ingredient needed to provide the claimed amount of dietary fibres, based on the specification of the specific ingredient provided by the supplier.

In one embodiment, the food composition of the present invention provides dietary fibres in an amount of at least 20.0 g per serving, for example at least 22.0 g per serving. In another embodiment, the food composition of the present invention provides dietary fibres in an amount ranging from 20.0 to 45.0 g per serving. In a further embodiment, the food composition of the present invention provides dietary fibres in an amount ranging from 22.0 to 40.0 g per serving.

In such embodiment, the food composition of the present invention delivers the daily amount of dietary fibres considered responsible for the observed increase in body weight loss.

In one embodiment, the food composition of the present invention provides dietary fibres in an amount of at least 3.5 g per serving, for example at least 4.0 g per serving. In another embodiment, the food composition of the present invention provides dietary fibres in an amount ranging from 3.50 to 7.0 g per serving. In a further embodiment, the food composition of the present invention provides dietary fibres in an amount ranging from 4.00 g to 6.00 g per serving.

In such embodiment, the food composition of the present invention delivers the daily amount of dietary fibres resulting to be missing in the general population according to our study and necessary to reach levels associated with the observed increase in body weight loss.

In one embodiment, the food composition according to the present invention may be administered in 1, 2, 3 or 4 daily servings to provide the total daily amounts of dietary fibres as above described. In such embodiment, as it will be apparent to a person skilled in the art, the amount of dietary fibres contained in each serving of the food composition according to the present invention will be divided by 1, 2 3 or 4 respectively.

In one embodiment, the food composition according to the present invention is consumed once or twice per day.

Health Benefits

In one aspect, the present invention provides for a food composition for use in assisting in post partum weight management.

In one embodiment, the recipient of the food composition of the present invention is a woman who gave birth earlier than the preceding 4 or 6 months. In one embodiment, such woman is in need of being assisted in postpartum weight management.

In one embodiment, the present invention provides for a food composition for use in assisting in post partum weight management in women in need thereof starting from 4 months after giving birth onwards.

In one embodiment, the present invention provides for a food composition for use in assisting in post partum weight management in women in need thereof starting from 6 months after giving birth onwards.

In another aspect, the present invention provides for a method of assisting in post partum weight management comprising administering to a woman in need thereof a food compositions of the present invention.

In one embodiment, the present invention provides for a method of assisting in post partum weight management comprising administering to a woman in need thereof a food compositions of the present invention starting from 4 months after giving birth onwards.

In another embodiment, the present invention provides for a method of assisting in post partum weight management comprising administering to a woman in need thereof a food compositions of the present invention starting from 6 months after giving birth onwards.

In one aspect, the present invention provides for use of at least one ingredient selected in the group consisting of ingredients delivering: zinc, magnesium, folates, Vitamin C, Thiamin, beta-carotene and dietary fibres in the manufacture of a food composition to assist in post partum weight management.

In one embodiment, the present invention provides for use of at least one ingredient selected in the group consisting of ingredients delivering: zinc, magnesium, folates, Vitamin C, Thiamin, beta-carotene and dietary fibres in the manufacture of a food composition to assist in post partum weight management in women starting from 4 months after giving birth onwards.

In another embodiment, the present invention provides for use of at least one ingredient selected in the group consisting of ingredients delivering: zinc, magnesium, folates, Vitamin C, Thiamin, beta-carotene and dietary fibres in the manufacture of a food composition to assist in post partum weight management in women starting from 6 months after giving birth onwards. In one embodiment of the present invention, assisting in post partum weight management occurs in a subject in need thereof for medical reasons and/or as a result of a medical condition. In one embodiment, weight management is linked to a medical condition.

In one embodiment of the present invention, assisting in post partum weight management occurs in a woman starting from 4 or 6 months after giving birth onward, such woman being in need thereof for medical reasons and/or as a result of a medical condition. In one embodiment, weight management is linked to a medical condition.

In one embodiment of the present invention, assisting post partum weight management is selected in the group consisting of: reducing body weight gain, improving and/or enhancing body weight loss and preventing post partum weight retention, in the women who gave birth, in particular when exclusive breast feeding is interrupted or breast feeding is reduced or stopped, for example starting from 6 or 4 months after giving birth onwards.

In another embodiment of the present invention, assisting post partum weight management is prevention and/or treatment of overweight and/or obesity in the women who gave birth, in particular when exclusive breast feeding is interrupted or breast feeding is reduced or stopped, for example starting from 6 or 4 months after giving birth onwards.

Non Therapeutic Use

In another aspect, the present invention provides for the non therapeutic use of a food composition comprising at least one ingredient selected in the group consisting of ingredients delivering: zinc, magnesium, folates, Vitamin C, Thiamin, beta-carotene and dietary fibres; to assist in post partum weight management.

In one embodiment, the present invention provides for the non therapeutic use of a food composition comprising at least one ingredient selected in the group consisting of ingredients delivering: zinc, magnesium, folates, Vitamin C, Thiamin, beta-carotene and dietary fibres; to assist in post partum weight management in women starting from 4 months after giving birth onwards.

In another embodiment, the present invention provides for the non therapeutic use of a food composition comprising at least one ingredient selected in the group consisting of ingredients delivering: zinc, magnesium, folates, Vitamin C, Thiamin, beta-carotene and dietary fibres; to assist in post partum weight management in women starting from 6 months after giving birth onwards.

Additional Embodiments According to the Present Invention a) Food composition comprising at least one ingredient selected in the group consisting of:
     dietary fibres;
     beta-carotene;
     folate;
     magnesium;
     zinc;
     Vitamin C; and
     Thiamin;
     For use in assisting in post partum weight management.
   b) Food composition for use according to embodiment a) comprising at least one ingredient selected in the group consisting of:
     dietary fibres in an amount of at least 3.5 g daily;
     folate in an amount of at least 90.0 µg daily;
     magnesium in an amount of at least 40.0 mg daily;
     beta-carotene in an amount of at least 0.70 mg daily;
     Thiamin in an amount of at least 0.40 mg daily;
     Vitamin C in an amount of at least 15 mg daily; and
     zinc in an amount of at least 1.0 mg daily.

c) Food composition for use according to embodiment a) or b) comprising at least one ingredient selected in the group consisting of:

dietary fibres in an amount ranging from 4.00 g to 6.00 g daily;

folate in an amount in an amount ranging from 100.0 to 140.0 µg daily;

magnesium in an amount ranging from 50.0 to 80.0 mg daily;

beta-carotene in an amount ranging from 0.75 to 0.90 mg daily;

Thiamin in an amount ranging from 0.45 to 0.60 mg daily;

Vitamin C in an amount ranging from 17.0 to 22.0 mg daily; and zinc in an amount ranging from 1.1 to 1.5 mg daily.

d) Food composition for use according to embodiment a) comprising at least one ingredient selected in the group consisting of:

fibres in an amount of at least 22.0 g daily;

folate in an amount of at least 350 µg daily;

magnesium in an amount of at least at least 340 mg daily;

beta-carotene in an amount of at least 3.0 mg daily;

Thiamin in an amount of at least 1.6 mg daily;

Vitamin C in an amount of at least 125.0 mg daily; and zinc in an amount of at least 10.5 mg daily.

e) Food composition for use according to embodiment a) or d) comprising at least one ingredient selected in the group consisting of:

fibres in an amount ranging from 22.0 to 40.0 g daily;

folate in an amount ranging from 370 and 480 µg daily;

magnesium in an amount ranging from 350 and 410 mg daily;

beta-carotene in an amount ranging from 3.2 and 4.0 mg daily;

Thiamin in an amount ranging from 1.8 to 2.3 mg daily;

Vitamin C in an amount ranging from 130.0 to 140.0 mg daily; and zinc in an amount in an amount ranging from 11.0 to 12.0 mg daily.

f) Food composition according to anyone of embodiments a) to e) for use in women starting from 4 months after delivery onwards.

g) Food composition according to anyone of embodiments a) to e) for use in women starting from 6 months after delivery onwards.

h) Food composition for use according to to anyone of embodiments a) to e) in a woman in need thereof for medical reasons and/or as a result of a medical condition.

i) Food composition comprising
fibres;
beta-carotene;
folate;
magnesium;
zinc;
Vitamin C; and
thiamin.

l) Food composition according to embodiment i) which comprises:

dietary fibres in an amount of at least 3.5 g daily;

folate in an amount of at least 90.0 µg daily;

magnesium in an amount of at least 40.0 mg daily;

beta-carotene in an amount of at least 0.70 mg daily;

Thiamin in an amount of at least 0.40 mg daily;

Vitamin C in an amount of at least 15 mg daily; and zinc in an amount of at least 1.0 mg daily.

m) Food composition according to embodiment i) or l) which comprises:

fibres in an amount ranging from 4.00 g to 6.00 g daily;

folate in an amount in an amount ranging from 100.0 to 140.0 µg daily;

magnesium in an amount ranging from 50.0 to 80.0 mg daily beta-carotene in an amount ranging from 0.75 to 0.90 mg daily;

Thiamin in an amount ranging from 0.45 to 0.60 mg daily;

Vitamin C in an amount ranging from 17.0 to 22.0 mg daily; and zinc in an amount ranging from 1.1 to 1.5 mg daily.

n) Food composition according to embodiment i) which comprises:

dietary fibres in an amount of at least 22.0 g daily;

folate in an amount of at least 350 µg daily;

magnesium in an amount of at least at least 340 mg daily;

beta-carotene in an amount of at least 3.0 mg daily;

Thiamin in an amount of at least 1.6 mg daily;

Vitamin C in an amount of at least 125.0 mg daily; and zinc in an amount of at least 10.5 mg daily.

o) Food composition according to embodiment i) or n) which comprises:

fibres in an amount ranging from 22.0 to 40.0 g daily;

folate in an amount ranging from 370 and 480 µg daily;

magnesium in an amount ranging from 350 and 410 mg daily;

beta-carotene in an amount ranging from 3.2 and 4.0 mg daily;

Thiamin in an amount ranging from 1.8 to 2.3 mg daily;

Vitamin C in an amount ranging from 130.0 to 140.0 mg daily and zinc in an amount in an amount ranging from 11.0 to 12.0 mg daily.

p) Food composition for use according to anyone of embodiment a) to g) or food composition according to anyone of embodiments h) to o) which also comprises conjugated Linolenic acid (CLA) glycerides, Vitamin E, Vitamin B6, calcium and which has a protein content higher than 15 g of protein per 100 g of food composition in a powder form.

q) Method for assisting post partum weight management comprising administering to a woman in need thereof a food composition as described in any of embodiment a) to p)

r) Non-therapeutic use of a food composition as described in anyone of embodiments i) to p) to assist in port partum weight management.

EXPERIMENTAL SECTION

Example 1

Identification of Clusters of Women Based on Dietary Pattern Analysis

Dietary data obtained from a dietary intake survey conducted in European mothers from several different countries were provided. The subjects were observed from the last visit immediately preceding their delivery (V0), and then observed for six follow-up visits after delivery, i.e. at day 2 (V1), 17 (V2), 30 (V3), 60 (V4), 90 (V5) and 120 (V6). At each visit, the subjects were asked to provide information on their dietary consumption over the immediately preceding three days. The dietary information was then translated to consumption data or food group data and nutrient daily intake by Nutrilog, using the French food group classification, which comprised 29 Food Groups and nutrient composition database (CIQUAL).

First step was to create a base dataset based on dietary patterns for further analysis, which involved two main steps: 1) removing outlier diets (daily diets which comprised less than 1074.8 kcal or more than 4776.9 kcal of total energy intake) and 2) removing subjects with insufficiently robust dietary information from selected visits.

Cluster analysis is the study of how to partition a set of items into non-overlapping groups, or clusters, such that items within a cluster are more similar to each other than to items in other clusters. In this report, we performed clustering on the 29 FoodGroup variables for the set of 180 subjects in the V2-V6 subset. Classical k-means algorithm was used to provide cluster assignments to each subject minimizing the total squared Euclidean distances between each point and its assigned cluster mean. As a result, four clusters were found and the nutrient intake of each cluster was calculated. Table 1 below reports the nutrients' mean daily intake and standard deviation for a subject in each cluster.

TABLE 1

| | Mean (std) of C0 | Mean (std) of C1 | Mean (std) of C2 | Mean (std) of C3 |
|---|---|---|---|---|
| Energy (kcal) | 2112.7 (441.3) | 1887.7 (330.7) | 2114.5 (399.5) | 2122.2 (293.1) |
| Proteins (g) | 82.9 (19.2) | 97.0 (15.4) | 81.3 (16.3) | 82.8 (12.7) |
| Fat (g) | 86.0 (20.9) | 59.7 (13.4) | 88.2 (20.1) | 85.6 (15.1) |
| Carbohydrates (g) | 237.2 (58.8) | 227.8 (46.7) | 233.8 (51.9) | 241.7 (37.5) |
| Alcohol (g) | 1.2 (2.0) | 0.5 (1.1) | 1.4 (2.1) | 1.3 (2.5) |
| Starch total (g) | 113.4 (37.7) | 119.6 (24.8) | 111.8 (30.9) | 115.9 (22.9) |
| Dietary fibre (g) | 25.1 (8.9) | 18.1 (4.9) | 19.9 (5.0) | 18.6 (4.6) |
| Sugars (g) | 95.7 (25.0) | 90.5 (29.0) | 97.5 (27.5) | 98.2 (24.7) |
| Selenium (µg) | 144.9 (60.3) | 173.1 (54.1) | 128.5 (59.0) | 112.8 (31.5) |
| Iodine (µg) | 168.6 (160.2) | 160.4 (37.5) | 159.2 (152.3) | 138.5 (51.1) |
| Potassium (mg) | 3373.6 (1345.6) | 3088.3 (610.8) | 2852.5 (652.2) | 2852.4 (723.2) |
| Phosphorus (mg) | 1390.9 (343.2) | 1328.8 (241.1) | 1339.5 (305.6) | 1308.7 (263.8) |
| Iron (mg) | 16.3 (18.1) | 8.6 (1.9) | 33.1 (120.6) | 12.3 (8.4) |
| Manganese (mg) | 4.8 (4.2) | 2.3 (0.6) | 3.4 (1.2) | 3.6 (4.1) |
| Copper (mg) | 1.8 (1.1) | 1.2 (0.3) | 1.8 (1.0) | 1.5 (0.5) |
| Calcium (mg) | 1077.3 (416.1) | 813.0 (287.9) | 1036.7 (419.8) | 967.1 (310.4) |
| Sodium (mg) | 2601.1 (652.9) | 2239.4 (585.0) | 2829.6 (559.5) | 3255.5 (1668.3) |
| Salt (g) | 3.9 (1.6) | 3.9 (1.2) | 3.6 (1.1) | 3.7 (1.4) |
| Magnesium (mg) | 380.0 (154.0) | 288.9 (59.3) | 341.4 (144.1) | 298.6 (67.8) |
| Zinc (mg) | 11.5 (8.1) | 9.3 (1.8) | 10.9 (7.9) | 9.7 (2.2) |
| Vitamin C (mg) | 134.4 (115.7) | 108.3 (49.3) | 126.7 (132.3) | 118.4 (69.0) |
| Niacin (mg) | 21.9 (16.8) | 23.0 (4.7) | 20.1 (17.1) | 19.5 (6.3) |
| Vitamin B6 (mg) | 2.2 (1.4) | 2.0 (0.4) | 2.0 (1.5) | 1.8 (0.6) |
| Vitamin B12 (µg) | 5.9 (3.2) | 7.7 (4.1) | 5.8 (4.2) | 6.9 (7.2) |
| Pantothenic acid (mg) | 5.9 (4.7) | 5.4 (1.1) | 5.9 (4.3) | 5.2 (2.0) |
| Folate, total (µg) | 446.2 (434.2) | 257.2 (62.9) | 378.4 (435.5) | 306.9 (89.9) |
| Riboflavin (mg) | 2.0 (1.7) | 1.7 (0.4) | 2.0 (1.6) | 1.8 (0.6) |
| Thiamin (mg) | 2.1 (2.4) | 1.3 (0.3) | 1.5 (1.5) | 1.5 (0.6) |
| Vitamin D (µg) | 6.2 (8.9) | 5.0 (1.8) | 5.6 (9.2) | 4.5 (4.5) |
| Vitamin E (mg) | 16.7 (24.6) | 7.2 (2.3) | 14.8 (25.4) | 11.4 (5.1) |
| Retinol (µg) | 398.4 (287.5) | 247.7 (96.5) | 496.0 (324.0) | 494.0 (463.9) |
| Vitamin A (µg_RE) | 940.2 (453.8) | 684.3 (266.1) | 930.3 (358.0) | 788.0 (435.8) |
| Beta-carotene (µg) | 3691.2 (2285.9) | 2657.0 (1507.7) | 3080.9 (2224.1) | 2094.7 (1009.8) |
| Fatty acid 4:0 (g) | 0.8 (0.3) | 0.6 (0.2) | 1.2 (0.5) | 1.0 (0.4) |
| Fatty acid 6:0 (g) | 0.6 (0.2) | 0.5 (0.2) | 0.8 (0.3) | 0.8 (0.4) |
| Fatty acid 8:0 (g) | 0.5 (0.2) | 0.4 (0.1) | 0.6 (0.2) | 0.6 (0.3) |
| Fatty acid 10:0 (g) | 0.8 (0.3) | 0.6 (0.2) | 1.1 (0.4) | 1.0 (0.5) |
| Fatty acid 12:0 (g) | 1.7 (1.0) | 1.0 (0.4) | 1.8 (0.6) | 2.0 (1.2) |
| Fatty acid 14:0 (g) | 3.2 (1.2) | 2.3 (0.7) | 3.9 (1.5) | 3.4 (1.2) |
| Fatty acid 16:0 (g) | 15.0 (4.1) | 12.1 (2.8) | 17.5 (5.0) | 16.2 (4.3) |
| Fatty acid 18:0 (g) | 5.9 (2.1) | 4.7 (1.4) | 7.3 (2.2) | 6.5 (1.9) |
| Fatty acid 18:1 cis omega-9 (g) | 27.1 (8.3) | 16.3 (4.6) | 23.6 (5.9) | 23.3 (4.7) |
| Fatty acid cis 18:2 omega-6 (g) | 8.1 (3.3) | 4.6 (1.3) | 6.8 (2.4) | 6.8 (1.9) |
| Fatty acid 18:3 omega-3 (ALA) (g) | 1.3 (0.8) | 0.7 (0.2) | 0.9 (0.3) | 1.0 (0.3) |
| Fatty acid 20:4 omega-6 (g) | 0.1 (0.0) | 0.1 (0.0) | 0.1 (0.0) | 0.1 (0.0) |
| Fatty acid 20:5 omega-3 (EPA) (g) | 0.2 (0.1) | 0.2 (0.2) | 0.2 (0.2) | 0.1 (0.1) |
| Fatty acid 22:6 omega-3 (DHA) (g) | 0.2 (0.2) | 0.4 (0.2) | 0.2 (0.2) | 0.2 (0.2) |
| saturated (SFA) (g) | 33.0 (9.2) | 24.3 (6.0) | 37.7 (11.0) | 35.6 (9.1) |
| monounsaturated (g) | 31.9 (8.8) | 19.6 (5.3) | 29.1 (6.9) | 28.6 (5.1) |
| polyunsaturated (g) | 11.7 (4.5) | 7.1 (1.9) | 10.5 (3.3) | 10.3 (2.7) |
| Cholesterol (mg) | 276.5 (76.5) | 318.1 (61.3) | 319.8 (121.4) | 298.3 (66.1) |
| Polyols (g) | 1.6 (1.5) | 1.6 (1.2) | 0.9 (1.0) | 1.0 (1.1) |
| Organic acids total (g) | 4.2 (1.5) | 3.9 (1.8) | 3.5 (1.6) | 3.5 (1.4) |

Example 2

Dietary Pattern and Post-Partum Weight Management

The body weight of each subject was measured on the day of first visit (day 2) and the day of the last visit (day 120), the difference, i.e. post-partum body weight loss was used in the analysis. To study the correlation with nutrient intakes and post-partum body weight loss, the latter was divided into tertiles, and classified as high (top ⅓), medium (middle ⅓) and low (bottom ⅓) body weight loss groups. The proportion of subjects classified as "high body weight loss" was compared among the 4 clusters.

It was observed that the highest proportion of subjects belonging to "high body weight loss" group was found in Cluster 0 (as above described) in which the average body weight loss was 12.6 kg while that of the other clusters was between 10-11 kg as shown in table 2. These findings are represented in FIG. 1 and indicate a potential role of certain nutrients abundant in the dietary pattern of Cluster 0 in assisting in post-partum body weight loss.

Surprisingly, the energy-adjusted amounts for some of the nutrients abundant in the Dietary pattern of Cluster 0 were found to correlate with the Mean Body weight loss over visits V2-V6.

Figure 2C:
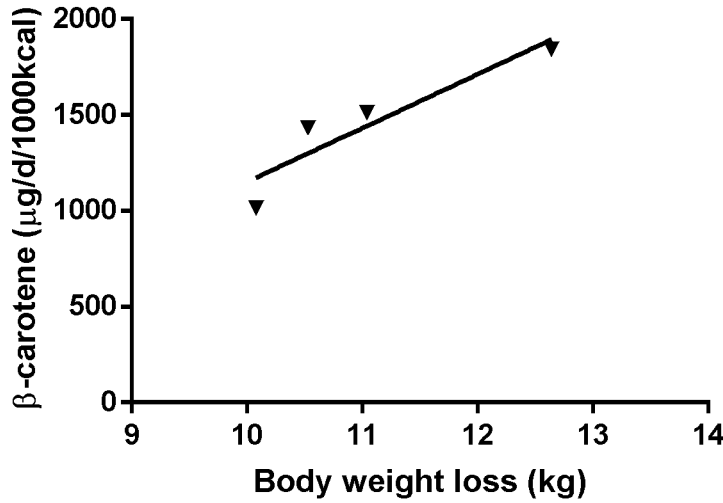
Figure 2D:
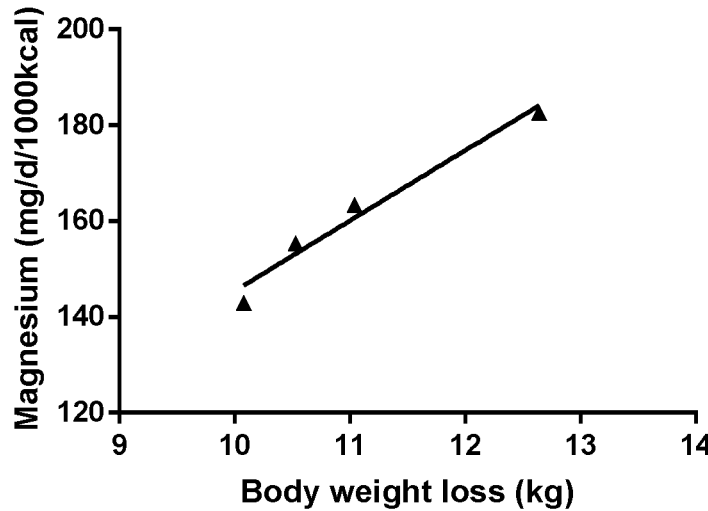
Figure 2E:
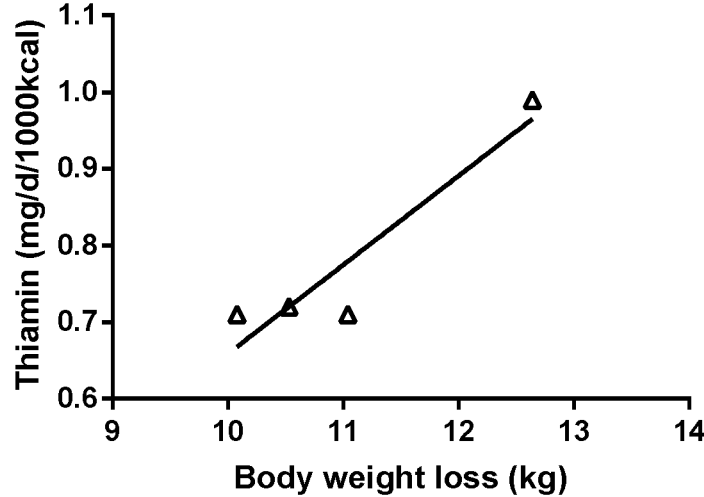
Figure 2F:
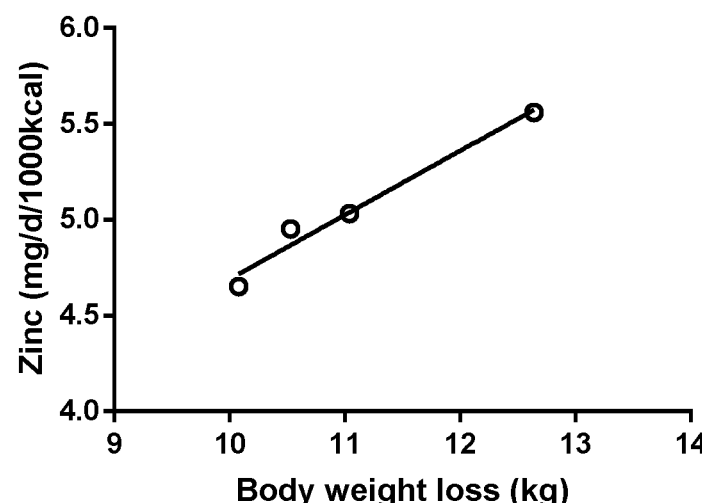
Figure 2G:
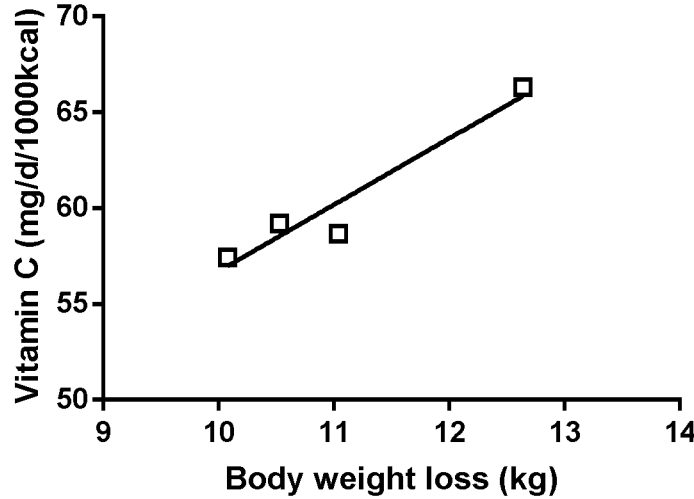

The nutrients whose amounts (Mean V2-V6, energy adjusted) were found to positively correlate with body weight loss (BWL, kg) in the study group are: Dietary fibre, beta-carotene, folate, magnesium, zinc, Vitamin C and thiamine. Table 2 here below details the results that are graphically represented in FIGS. 2a to 2g.

TABLE 2

| | BWL | Dietary fibre_g | Folate_total_ug | Beta_carotene_ug | Magnesium_mg | Thiamin, mg | Zinc_mg | Vitamin_C_mg |
|---|---|---|---|---|---|---|---|---|
| Cluster 1 | 12.64 | 12.07 | 220.12 | 1840.27 | 182.62 | 0.99 | 5.56 | 66.32 |
| Cluster 2 | 10.53 | 9.75 | 138.72 | 1433.11 | 155.27 | 0.72 | 4.95 | 59.21 |
| Cluster 3 | 11.04 | 9.6 | 174.06 | 1511.95 | 163.33 | 0.71 | 5.03 | 58.68 |
| Cluster 4 | 10.08 | 8.85 | 147.17 | 1014.72 | 142.99 | 0.71 | 4.65 | 57.42 |
| P value | | 0.027 | 0.0378 | 0.0757 | 0.0162 | 0.0647 | 0.0135 | 0.037 |

Accordingly, without wishing to be bound by theory, the present inventors believe that the above mentioned nutrients have a role in assisting weight management, in particular post-partum weight management and that they can promote prevention of post-partum weight retention in female who gave birth.

This results particularly advantageous after 6 months from delivery and onwards, when the innate energy consumption provided by lactation (especially exclusive breastfeeding) decreases due to diminished breastfeeding sessions and/or breastfeeding interruption. Surprisingly, other nutrients present in high amounts in the Diet of Cluster 0 and known in the state of the art to promote body weight loss in obese subjects (such as for example Monounsaturated Fatty acids) didn't result to correlate with body weight loss in the studied population. Also surprisingly, Vitamin D or Vitamin E which are also nutrients known in the state of the art to promote body weight loss in obese subjects, didn't result to be present in high amounts in the diet of women of Cluster 0 who showed a higher body weight loss compared to the other identified clusters of lactating women.

Example 3

Identification of Amounts of Nutrients to be Supplemented

In order to quantify the amounts of the above mentioned nutrients which should be supplemented in the general population to assist in post-partum weight management, the present inventors compared the mean levels found for such nutrients in the subjects of Cluster 0 with those representative of the general population (clusters 0 to 3 considered all together). The resulting difference is representative of such amounts to be supplemented in the general population of women who gave birth.

Results are reported in table 3 below.

TABLE 3

| Raw daily intake (per day) | Mean for General Population (C0-C3) | St. Dev | Mean of CO (High body weight loss) | SD | Difference between general population and high body weight loss cluster |
|---|---|---|---|---|---|
| Dietary fibre (g) | 20.16 | 6.53 | 25.1 | -8.9 | 4.94 |
| Magnesium (mg) | 322.63 | 114.05 | 380 | -154 | 57.37 |
| Zinc (mg) | 10.22 | 5.5 | 11.5 | -8.1 | 1.28 |
| Vitamin C (mg) | 120.5 | 92.54 | 134.4 | -115.7 | 13.9 |
| Folate, total (µg) | 337.21 | 297.98 | 446.2 | -434.2 | 108.99 |
| Thiamin (mg) | 1.58 | 1.38 | 2.1 | -2.4 | 0.52 |
| Beta-carotene (µg) | 2835.77 | 1856.71 | 3691.2 | -2285.9 | 855.43 |

Example 4

Dairy Food Composition

A dairy product according to the present invention may be prepared by incorporation into a dairy based matrix providing 300 kcal of the following nutrients:

Thiamin 0.75 (mg)
Folate 160 (µg DEF)
Zinc 2.8 (mg)
Magnesium 78 (mg)
Dietary fibre 7.5 g
Beta-carotene 1300 (µg)
Vitamin C 32 (mg)

The product is intended for daily consumption (one serving per day) and may assist in the post-partum weight management and prevention of post-partum weight retention, in particular from 6 months after delivery onwards.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

The invention claimed is:

1. A method for assisting in post-partum weight management in a women in need of post-partum weight management, the method comprising administering to the individual a food composition comprising at least one ingredient selected from the group consisting of: dietary fibers in an amount of at least 3.5 g per serving; folate in an amount of at least 90.0 mg per serving;

magnesium in an amount of at least 40.0 mg per serving;
        beta-carotene in an amount of at least 0.70 mg per serving; Thiamin in an amount of at least 0.40 mg per serving;
    Vitamin C in an amount of at least 15 mg per serving; and
        zinc in an amount of at least 1.0 mg per serving, wherein the food composition does not contain probiotics.

2. The method according to claim 1, wherein the food composition comprises at least one ingredient selected from the group consisting of:
    dietary fibers in an amount ranging from 4.00 g to 6.00 g per serving;
    folate in an amount in an amount ranging from 100.0 to 140.0 mg per serving;

magnesium in an amount ranging from 50.0 to 80.0 mg per serving;
    beta-carotene in an amount ranging from 0.75 to 0.90 mg per serving;
    Thiamin in an amount ranging from 0.45 to 0.60 mg per serving;
    Vitamin C in an amount ranging from 17.0 to 22.0 mg per serving; and
    zinc in an amount ranging from 1.1 to 1.5 mg per serving.

3. The method according to claim 1, wherein the food composition comprises at least one ingredient selected from the group consisting of:
    fibers in an amount of at least 22.0 g per serving;
    folate in an amount of at least 350 mg per serving;
    magnesium in an amount of at least at least 340 mg per serving;
    beta-carotene in an amount of at least 3.0 mg per serving;
    Thiamin in an amount of at least 1.6 mg per serving;
    Vitamin C in an amount of at least 125.0 mg per serving; and
    zinc in an amount of at least 10.5 mg per serving.

4. The method according to claim 1, wherein the food composition comprises at least one ingredient selected in the group consisting of:
    fibers in an amount ranging from 22.0 to 40.0 g per serving;
    folate in an amount ranging from 370 and 480 mg per serving;
    magnesium in an amount ranging from 350 and 410 mg per serving;
    beta-carotene in an amount ranging from 3.2 and 4.0 mg per serving;
    Thiamin in an amount ranging from 1.8 to 2.3 mg per serving;
    Vitamin C in an amount ranging from 130.0 to 140.0 mg per serving; and
    zinc in an amount in an amount ranging from 11.0 to 12.0 mg per serving.

5. The method according to claim 1, wherein the individual is a woman at least 4 months post-partum.

6. The method according to claim 1, wherein the individual is a woman at least 6 months post-partum.

7. The method according to claim 1, wherein the individual is a woman in need of post-partum weight management for medical reasons and/or as a result of a medical condition.

* * * * *